(12) United States Patent
Chang et al.

(10) Patent No.: US 9,718,891 B2
(45) Date of Patent: Aug. 1, 2017

(54) ANTIBODIES SPECIFIC TO A NOVEL EPITOPE ON CεMX OF HUMAN MEMBRANE-BOUND IGE AND USES THEREOF IN TREATING IGE-MEDIATED DISEASES

(71) Applicant: Academia Sinica, Taipei (TW)

(72) Inventors: Tse Wen Chang, Taipei (TW); Chien-Jen Lin, Taipei (TW); Chien-Sheng Lu, Kaohsiung (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/775,204

(22) PCT Filed: Mar. 12, 2014

(86) PCT No.: PCT/US2014/024172
§ 371 (c)(1),
(2) Date: Sep. 11, 2015

(87) PCT Pub. No.: WO2014/165028
PCT Pub. Date: Oct. 9, 2014

(65) Prior Publication Data
US 2016/0032017 A1    Feb. 4, 2016

Related U.S. Application Data

(60) Provisional application No. 61/779,271, filed on Mar. 13, 2013.

(51) Int. Cl.
*A61K 39/395* (2006.01)
*C07K 16/42* (2006.01)
*C07K 7/04* (2006.01)

(52) U.S. Cl.
CPC ............ *C07K 16/4291* (2013.01); *C07K 7/04* (2013.01); *C07K 2317/34* (2013.01); *C07K 2317/52* (2013.01); *C07K 2317/73* (2013.01)

(58) Field of Classification Search
None
See application file for complete search history.

(56) References Cited

U.S. PATENT DOCUMENTS

| | | | | |
|---|---|---|---|---|
| 5,958,708 A | * | 9/1999 | Hardman | ......... A61K 47/48653 435/7.21 |
| 6,172,213 B1 | * | 1/2001 | Lowman | .......... A61K 39/39566 435/252.3 |
| 6,685,939 B2 | * | 2/2004 | Jardieu | ................... C07K 16/00 424/130.1 |
| 2009/0010924 A1 | | 1/2009 | Wu et al. | |

FOREIGN PATENT DOCUMENTS

| | | | | |
|---|---|---|---|---|
| CN | WO 2010097012 A1 | * | 9/2010 | ......... C07K 16/4291 |
| WO | WO 2008116149 A2 | * | 9/2008 | ......... A01K 67/0278 |
| WO | WO 2010/097012 A1 | | 9/2010 | |

OTHER PUBLICATIONS

Janeway et al., Immunobiology, 3rd edition, 1997, Garland Publishing Inc., pp. 3:1-3:11.*
Rudikoff et al., Proc Natl Acad Sci U S A. Mar. 1982;79(6):1979-83.*
Portolano et al., J Immunol. Feb. 1, 1993;150(3):880-7.*
Paul, William E (editor) Fundamental Immunology, 3rd ed. 1993, p. 242.*
Genbank Submission; NIH/NCBI, Accession No. BAE71466. Furukama et al., Jan. 6, 2006. 2 pages.
Genbank Submission; NIH/NCBI, Accession No. AER46505. Kuwata, Nov. 6, 2011. 2 pages.
MacGlashan DW, Jr. IgE-dependent signaling1 as a therapeutic target for allergies. Trends Pharmacol Sci. Sep. 2012;33(9):502-9. doi: 10.1016/j.tips.2012.06.002. Epub Jun. 30, 2012. Review.
Wagner et al., Monoclonal anti-equine IgE antibodies with specificity for different epitopes on the immunoglobulin heavy chain of native IgE. Vet Immunol Immunopathol. Mar. 20, 2003;92(1-2):45-60.
Wan et al., Genetic variations in the CεmX domain of human membrane-bound IgE. Immunogenetics. Jan. 8, 2010;62:273-80. Epub Mar. 24, 2010.

* cited by examiner

*Primary Examiner* — Michael Szperka
(74) *Attorney, Agent, or Firm* — Wolf, Greenfield & Sacks, P.C.

(57) ABSTRACT

The present disclosure relates to anti-IgE antibodies that bind to novel antigenic epitopes of the CsmX domain, e.g., SVPHPRCHCGAGRA (SEQ ID NO: 4) and the uses thereof in treating IgE-mediated diseases.

22 Claims, 5 Drawing Sheets

Figure 4

V_H domain

```
                    10                  20                  30
23B11       E V Q L Q Q S G A E L M K P G A S V K I S C K A S G Y T F S
HV1         Q V Q L Q Q S G A E L M K P G A S V K L S C K T S G Y T F T 31 a            40                  50   52 a
23B11       S Y W I E W V Y Q R P G H G L E W I G E I L P G S G S S N Y
HV1         G Y W I E W V K Q R P G H G L E W I G E I L P G S G S T N Y 60                  70                80  82 a b
23B11       N E K F E G K A T F T A D T S S N T A Y M H L S S L T S E D
HV1         N E K F K G K A T F T A D T S S N T A Y M Q L S S L T T E D 90              100 a b c d                110
23B11           S A V Y Y C A R W D Y Y G G R G F D Y W G Q G T T L T A A A
HV1/HD1/HJ2     S A I Y Y C A R W D Y Y G G R G F D Y W G Q G T T L T A A A
```

V_L domain

```
                    10                  20                  30
23B11       D I V M T Q A A P S V P V T P G E S V S I S C R S S K S L L
KV2         D I V M T Q A A P S V P V T P G E S V S I S C R S S K S L L a b c d e           40                  50
23B11       H S N G N I Y L H W F L Q R P G Q S P Q L L I Y R M S N V A
KV2         H S N G N T Y L Y W F L Q R P G Q S P Q L L I Y R M S N L A 60                  70                  80
23B11       S G V P D R F S G S G S G T V F T L R I S R V E A E D V G V
KV2         S G V P D R F S G S G S G T A F T L R I S R V E A E D V G V 90                  100        106 a
23B11       Y Y C M Q N L E Y P L T F G A G T K L E L K
KV2/KJ5     Y Y C M Q H L E Y P L T F G A G T K L E L K
```

ANTIBODIES SPECIFIC TO A NOVEL EPITOPE ON CεMX OF HUMAN MEMBRANE-BOUND IGE AND USES THEREOF IN TREATING IGE-MEDIATED DISEASES

RELATED APPLICATION

This application is a national stage filing under 35 U.S.C. §371 of international PCT application PCT/US2014/024172, filed Mar. 12, 2014, which claims the benefit of U.S. provisional application No. 61/779,271, filed Mar. 13, 2013 under 35 U.S.C. §119, each of which is herein incorporated by reference in its entirety.

BACKGROUND OF THE INVENTION

Immunoglobulin E (IgE) plays a central role in mediating type I hypersensitivity reactions that are responsible for causing allergic diseases, including allergic asthma, allergic rhinitis, atopic dermatitis, peanut allergy, latex allergy, and others. Allergic reactions are the responses of the immune system toward harmless environmental substances, such as dust mites, tree and grass pollens, certain food and drugs, and bee and fire ant bites. In such reactions, the binding of an allergen to IgE on the surface of basophils and mast cells causes the cross-linking of IgE and the aggregation of the underlying receptors of IgE.Fc, the type I IgE.Fc receptors, or FcεRI. This receptor aggregation subsequently activates the signaling pathway leading to the exocytosis of granules and the release of pharmacologic mediators, such as histamine, leukotrienes, tryptase, cytokines and chemokines. The release of those mediators from mast cells and basophils causes the various pathological manifestations of allergy.

Anti-IgE antibodies binding to free IgE in the blood and in interstitial fluid and to mIgE on B cells, but not to IgE bound by FcεRI on basophils and mast cells, such as omalizumab and TNX-901, have been developed for treating IgE-mediated allergic diseases. These antibodies bind to IgE with high affinity at a site in the CH3 domain of Fc that overlaps with the binding site of FcεRI. Hence, the anticipated therapeutic effects of these antibodies are based on the binding of the antibodies to free IgE and to mIgE on B lymphoblasts and on memory B cells, which leads to the reduction of overall free IgE level in blood and interstitial fluid.

The clinical development of omalizumab (trade name Xolair) has shown additional multiple pharmacologic effects in attenuating type I hypersensitivity in various allergic indications. The binding of anti-IgE to free IgE further prevents IgE binding to FcεRI on the surface of basophils and mast cells. As the FcεRI unoccupied by IgE is unstable and subsequently internalized and degraded, the depletion of free IgE with anti-IgE binding also gradually down-regulates FcεRI on basophils and mast cells. Evidence for other effects of the antibody therapy has been found, including the neutralization of cytokinergic activities, the attenuation of overall inflammatory activity, and possibly the sweeping of allergens through the accumulation of IgE-anti-IgE immune complexes.

CεmX is a 52-amino acid segment located between the CH4 domain and the C-terminal membrane-anchoring segment of human membrane-bound ε chain (mε). It has been shown that in most human subjects studied, the mε without CεmX (mεS) accounts for minute proportions, whereas mε chain with CεmX (mεL) is dominantly expressed. The mRNAs for ε chain of free, secreted IgE and for mεS and mεL of mIgE are all derived from alternative splicing of the ε RNA transcript. The amino acid and nucleotide sequences of CεmX are unique in the entire protein and DNA databases. Therefore, CεmX provides a unique antigenic site for targeting mIgE and the mIgE-expressing B cells.

Anti-IgE antibodies binding to the CεmX (also known as the M1' region or M1' peptide), which exists on human mIgE for the targeting of mIgE-expressing B lymphocytes, have also been developed. See, e.g., Chen et al., *J. Immunol.*, 184: 1748-1756, 2010; U.S. Pat. No. 8,071,097; and WO2010/097012.

It is of great interest to identify new antigenic epitopes within the CεmX domain and develop new therapeutic antibodies binding to such antigenic epitopes.

SUMMARY OF THE INVENTION

The present disclosure is based on the surprising discovery of a discrete linear antigenic motif AAGGSVPHPRCHCGAGRA (SEQ ID NO:1), spanning amino acid residues 29-46 of the CεmX domain of IgE, and the development of at least one monoclonal antibody that is capable of binding to that motif and is effective in inducing antibody-dependent cellular toxicity (ADCC) and apoptosis in membrane-bound IgE-expressing B cells. The accessibility of this newly discovered antigenic motif to antibody binding was not predictable because this 18 amino acid-long segment overlaps with two amino acid residues of the C-terminal segment of CεmX (i.e., RADWPGPP, SEQ ID NO:7), which is known to be hindered from antibody binding.

Accordingly, one aspect of the present disclosure features an isolated an isolated anti-IgE antibody that binds to AAGGSVPHPRCHCGAGRA (SEQ ID NO:1), or an antigenic epitope therein, e.g., SVPHPRCHCGAGRA (SEQ ID NO:4). This anti-IgE antibody can be a full-length antibody or an antigen-binding fragment thereof, which includes, but is not limited to, a Fab fragment, a F(ab')2 fragment, or a single-chain Fv fragment. The anti-IgE antibody described herein is can also be a human antibody, a humanized antibody, a chimeric antibody, or a single-chain antibody.

In some embodiments, the anti-IgE antibody described herein comprises a heavy chain variable region ($V_H$) that comprises a $V_H$ complementarity determining region (CDR) 1 set forth as SEQ ID NO:12, a $V_H$ CDR2 set forth as SEQ ID NO:13, and a $V_H$ CDR3 set forth as SEQ ID NO:14. Alternatively or in addition, the anti-IgE antibody can comprise a light chain variable region ($V_L$) that comprises a $V_L$ CDR1 set forth as SEQ ID NO:15, a $V_L$ CDR2 set forth as SEQ ID NO:16, and a $V_L$ CDR3 set forth as SEQ ID NO:17.

In other embodiments, the antibody comprises a $V_H$ that is at least 85% (e.g., 90%, 95%, 97%, 98%, or 99%) identical to SEQ ID NO:8. Alternatively or in addition, the anti-IgE antibody comprises a $V_L$ that is at least 85% (e.g., 90%, 95%, 97%, 98%, or 99%) identical to SEQ ID NO:9. The anti-IgE antibody binds to the same epitope as an anti-IgE antibody having a $V_H$ set forth as SEQ ID NO:8 and a $V_L$ set forth as SEQ ID NO:9. In one example, the anti-IgE antibody comprises a $V_H$ set forth as SEQ ID NO:8 and a $V_L$ set forth as SEQ ID NO:9.

In yet another aspect, the present disclosure provides an isolated nucleic acid comprising a nucleotide sequence encoding an antibody heavy chain variable region ($V_H$) that comprises a $V_H$ complementarity determining region (CDR) 1 set forth as SEQ ID NO:12, a $V_H$ CDR2 set forth as SEQ ID NO:13, and a $V_H$ CDR3 set forth as SEQ ID NO:14, and/or a nucleotide sequence encoding an antibody light chain variable region ($V_L$) that comprises a $V_L$ complementarity determining region (CDR1) set forth as SEQ ID NO:15, a $V_L$ CDR2 set forth as SEQ ID NO:16, and a $V_L$ CDR3 set forth as SEQ ID NO:17. Also provided here are vectors (e.g., expression vectors) comprising any of the nucleic acids described herein, and host cells comprising such vectors. In some examples, a vector (e.g., an expression vector) described herein comprises nucleotide sequences encoding both the heavy chain and light chain of any of the anti-IgE antibodies described herein. In other examples, the nucleotide sequences encoding the heavy chain and light chain are located on different vectors.

In another aspect, the present disclosure provides methods for preparing any of the anti-IgE antibodies described herein, the methods comprising culturing a host cell comprising expression vector(s) encoding the heavy and light chains of the antibody, and collecting the cultured cells for purification of the antibodies thus produced. Such a method can further comprise isolating the antibodies from either the cultured cells or the culture medium.

Further, the present disclosure provides compositions (e.g., pharmaceutical compositions) comprising any of the anti-IgE antibodies described herein or any of the nucleic acids or vectors described herein, and a carrier, such as a pharmaceutically acceptable carrier.

In addition, the present disclosure provides an immune composition comprising a peptide and an adjuvant, wherein the peptide comprises the amino acid sequence of AAGGSVPHPRCHCGAGRA (SEQ ID NO:1) or any immunogenic epitope therein, e.g., SVPHPRCHCGAGRA (SEQ ID NO:4). In some examples, the peptide is conjugated to a carrier. Such immune compositions can be used to elicit immune responses specific to the peptide.

In yet another aspect, the present disclosure features a method of treating an IgE-mediated condition in a subject, the method comprising administering to a subject in need thereof an effective amount of (i) any of compositions described herein, which comprises any of the anti-IgE antibodies or nucleic acids encoding such, or (ii) any of the immune compositions described herein, which comprises a peptide of AAGGSVPHPRCHCGAGRA (SEQ ID NO:1) or any immunogenic epitope therein, e.g., SVPHPRCHCGAGRA (SEQ ID NO:4).

Examples of IgE-mediated conditions include, but are not limited to, cold-induced urticaria, chronic urticaria, cholinergic urticaria, chronic rhinosinusitis, systemic mastocytosis, cutaneous mastocytosis, allergic bronchopulmonary aspergillosis, recurrent idiopathic angioedema, interstitial cystitis, an eosinophil-associated gastrointestinal disorder, allergic asthma, allergic rhinitis or atopic dermatitis. In some examples, the IgE-mediated condition is allergic asthma, allergic rhinitis or atopic dermatitis.

The subject in need of the treatment described herein can be a subject (e.g., a human patient) having or suspected of having an IgE-mediated condition.

Also within the scope of the present disclosure are pharmaceutical compositions or immune compositions for use in treating an IgE-mediated disease, such as those listed above. The pharmaceutical composition comprising any of the anti-IgE antibodies or nucleic acid encoding such and a pharmaceutically acceptable carrier. The immune compositions comprises at least a peptide of AAGGSVPHPRCHCGAGRA (SEQ ID NO:1) or any immunogenic epitope therein, e.g., SVPHPRCHCGAGRA (SEQ ID NO:4), and optionally an adjuvant. Further, the present disclosure includes uses of such pharmaceutical or immune compositions in manufacturing a medicament for treating the IgE-mediated disease.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

FIG. 4 shows the amino acid sequences of murine mAb 23B11 V$_H$ domain (SEQ ID NO:8) and V$_L$ domain (SEQ ID NO:9), as compared to murine consensus sequences of heavy chain subgroup 1 (HV1) (SEQ ID NO:10) and light chain κ subgroup 13 (KV2) (SEQ ID NO:11), respectively. The three CDRs in each chain are underlined. V$_H$ CDR1: SEQ ID NO:12; V$_H$ CDR2: SEQ ID NO:13; and V$_H$ CDR3: SEQ ID NO:14; V$_L$ CDR1: SEQ ID NO:15; V$_L$ CDR2: SEQ ID NO:16; V$_L$ CDR3: SEQ ID NO:17.

DETAILED DESCRIPTION OF THE INVENTION

Figure 1:
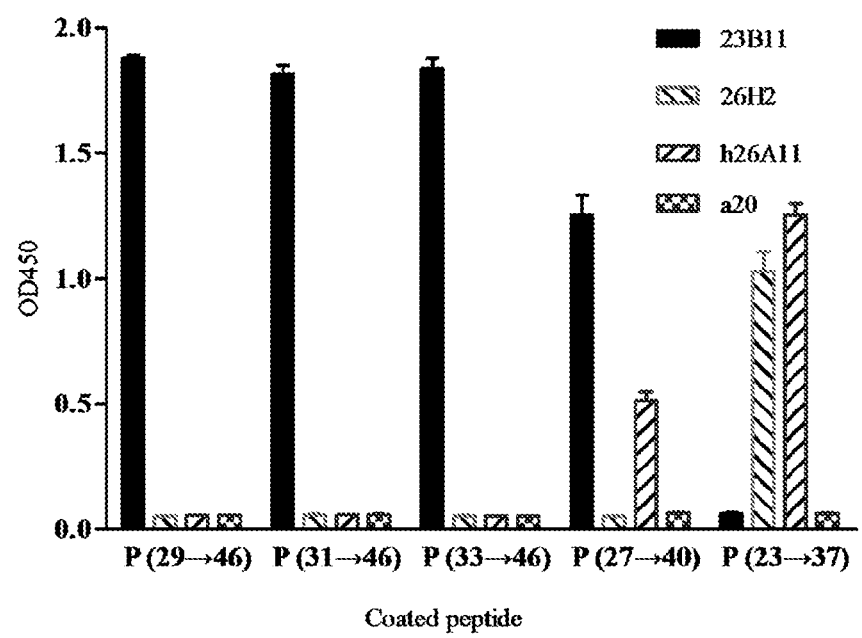
FIG. 1 shows the binding activity of monoclonal antibody mAb 23B1 to various peptides derived from CϵmX. A: the amino acid sequence of the CϵmX domain (SEQ ID NO:2) and other synthetic peptide sequences spanning the CϵmX domain (top to bottom, SEQ ID NOs: 1 and 3-6). B: a graph representing the reactivity of mAb 23B11, mAb 26H2, mAb h26A11 and mAb a20 with the various synthetic CϵmX peptide segments, as determined by enzyme-linked immunosorbent assay (ELISA).

The present disclosure reports the unexpected identification of an antigenic segment, AAGGSVPHPRCHCGAGRA (SEQ ID NO:1), present in the CϵmX domain (SEQ ID NO:2) of membrane-bound IgE on B cells. Monoclonal antibody 23B11 (mAb 23B11), which is capable of binding to an antigenic epitope located in this segment, effectively induced apoptosis and ADCC in B cells expressing membrane-bound IgE. Other anti-IgE monoclonal antibodies known in the art (e.g., mAb a20, mAb 4B12, mAb 26H2, mAb 47H4, mAb 7A6 and mAb 26A11) do not bind this antigenic segment. See U.S. Pat. Nos. 8,460,664 and 8,071,097.

Accordingly, the present disclosure provides isolated antibodies capable of binding to AAGGSVPHPRCHCGAGRA (SEQ ID NO:1), or an antigenic epitope therein (e.g., SEQ ID NO:4), nucleic acids encoding the heavy and light chains of the antibody, pharmaceutical compositions comprising any of the anti-IgE antibodies or nucleic acids encoding such, methods for producing such antibodies, and methods of treating IgE-mediated diseases using any of the antibodies or encoding nucleic acids. Also within the scope of the present disclosure are immunological compositions comprising the antigenic peptide AAGGSVPHPRCHCGAGRA (SEQ ID NO:1), or an antigenic epitope therein, and uses thereof in treating any of the anti-IgE antibodies described herein.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature such as, for example, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Anti-IgE Antibodies

Membrane-bound IgE (mIgE) on B cells plays a critical role in isotype-specific IgE responses. On mIgE B cells, the membrane-bound ε-chain (mε) exists predominantly in the long isoform, mεL, containing an extra 52 amino acid CεmX domain between CH4 and the C-terminal membrane-anchoring segment; the short isoform of mε, mεS, exists in minor proportions. Thus, CεmX is an attractive site for immunologic targeting of mIgE B cells.

Described herein are isolated anti-IgE antibodies targeting specific segments within the CεmX domain. The term "isolated antibody" used herein refers to an antibody substantially free from naturally associated molecules, i.e., the naturally associated molecules constituting at most 20% by dry weight of a preparation containing the antibody. Purity can be measured by any appropriate method, e.g., column chromatography, polyacrylamide gel electrophoresis, and HPLC.

An antibody (interchangeably used in plural form) is an immunoglobulin molecule capable of specific binding to a target such as, for example, a carbohydrate, polynucleotide, lipid or polypeptide through at least one antigen recognition site located in the variable region of the immunoglobulin molecule. As used herein, the term "antibody" encompasses not only intact (e.g., full-length) polyclonal or monoclonal antibodies, but also antigen-binding fragments thereof (such as Fab, Fab', F(ab')$_2$ and Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins may be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma and mu, respectively. The subunit structures and three-dimensional configurations of different classes of immunoglobulins are well known.

The anti-IgE antibodies described herein, which are useful in alleviating IgE-mediated diseases, may be murine, rat, human or any other origin (including chimeric or humanized antibodies). In some examples, the antibodies comprise a modified constant region, such as a constant region that is immunologically inert, e.g., does not trigger complement mediated lysis or does not stimulate antibody-dependent cell mediated cytotoxicity (ADCC). ADCC activity may be assessed using methods disclosed in U.S. Pat. No. 5,500,362. In other embodiments, the constant region is modified as described in *Eur. J. Immunol.* (1999) 29:2613-2624; PCT Application No. PCT/GB99/01441; and/or UK Patent Application No. 9809951.8.

Any of the antibodies described herein may be either monoclonal or polyclonal. A "monoclonal antibody" refers to a homogenous antibody population, and a "polyclonal antibody" refers to a heterogeneous antibody population. These two terms do not limit the source of an antibody or the manner in which it is made.

In some embodiments, the antibodies provided herein are humanized antibodies. Humanized antibodies may refer to forms of non-human (e.g., murine) antibodies that are specific chimeric immunoglobulins, immunoglobulin chains or antigen-binding fragments thereof that contain minimal sequence derived from non-human immunoglobulin. Humanized antibodies may be human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some embodiments, Fv framework region (FR) residues of the human immunoglobulin are replaced by corresponding non-human residues. Furthermore, the humanized antibodies may comprise residues that are found neither in the recipient antibodies nor in the imported CDR or framework sequences, but are included to further refine and optimize antibody performance. In some embodiments, humanized antibodies may comprise substantially all of at least one or two, variable domains, in which all or substantially all of the CDR regions correspond to those of non-human immunoglobulins and all or substantially all of the FR regions are those of a human immunoglobulin consensus sequence. The humanized antibodies may also comprise at least a portion of an immunoglobulin constant region or domain (Fc), typically that of a human immunoglobulin. Antibodies may have Fc regions modified as described in WO 99/58572. Other forms of humanized antibodies may have at least one CDR (one, two, three, four, five, six), which may be altered with respect to the original antibodies, which is also termed at least one CDR "derived from" at least one CDR from the original antibody. Humanized antibodies may also involve affinity maturation.

In some embodiments, the antibodies described herein are chimeric antibodies, which can include a heavy constant region and a light constant region from human antibodies. Chimeric antibodies may refer to antibodies having a variable region or part of variable region from a first species and a constant region from a second species. In some embodiments, in these chimeric antibodies, the variable region of both light and heavy chains may mimic the variable region of antibodies derived from one species of mammal (e.g., a non-human mammal such as mouse, rabbit and rat), while the constant portions may be homologous to the sequences in antibodies derived from another mammal such as a human. In some embodiments, amino acid modifications may be made in the variable region and/or the constant region.

The antibodies disclosed herein are capable of binding to a newly identified antigenic segment of CεmX, i.e., AAGGSVPHPRCHCGAGRA (SEQ ID NO:1), or an antigenic epitope therein (e.g., SEQ ID NO:4). Such antibodies may be capable of binding to the just-noted antigenic segment/epitope located in the CεmX domain of membrane-bound IgE (mIgE) on B lymphocytes (e.g., human B lymphocytes or B cells).

In some embodiments, the anti-IgE antibodies described herein specifically and/or preferentially bind to the antigenic CεmX segment or epitopes therein. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to the antigenic segment AAGGSVPHPRCHCGA-GRA (SEQ ID NO:1) is an antibody that binds to this IgE segment with greater affinity, avidity, more readily and/or with greater duration than it binds to other IgE epitopes or non-IgE epitopes. In some embodiments, an antibody that specifically binds to a first target antigen may or may not specifically or preferentially bind to a second target antigen. As such, "specific binding" or "preferential binding" does not necessarily require (although it can include) exclusive binding. In some embodiments, reference to binding means preferential binding.

An anti-IgE antibody of the present disclosure may be an antibody that bind to (e.g., specifically binds to) the antigenic segment AAGGSVPHPRCHCGAGRA (SEQ ID NO:1) of IgE. An anti-IgE antibody of the present disclosure may also be an antibody that binds to an antigenic epitope within AAGGSVPHPRCHCGAGRA (SEQ ID NO:1). For example, an anti-IgE antibody of the present disclosure may specifically bind to one of the following fragments of SEQ ID NO:1: AGGSVPHPRCHCGAGRA (SEQ ID NO:18); GGSVPHPRCHCGAGRA (SEQ ID NO:3); GSVPHPRCH-CGAGRA (SEQ ID NO:20); SVPHPRCHCGAGRA (SEQ ID NO:4); VPHPRCHCGAGRA (SEQ ID NO:22); PHPRCHCGAGRA (SEQ ID NO:23); HPRCHCGAGRA (SEQ ID NO:24); PRCHCGAGRA (SEQ ID NO:25); RCH-CGAGRA (SEQ ID NO:26); CHCGAGRA (SEQ ID NO:27); HCGAGRA (SEQ ID NO:28); CGAGRA (SEQ ID NO:29); GAGRA (SEQ ID NO:30); AGRA (SEQ ID NO:31); AGGSVPHPRCHCGAGR (SEQ ID NO:32); AGGSVPHPRCHCGAG (SEQ ID NO:33); AGGSVPH-PRCHCGA (SEQ ID NO:34); AGGSVPHPRCHCG (SEQ ID NO:35); AGGSVPHPRCHC (SEQ ID NO:36); AGGS-VPHPRCH (SEQ ID NO:37); AGGSVPHPRC (SEQ ID NO:38); AGGSVPHPR (SEQ ID NO:39); AGGSVPHP (SEQ ID NO:40); AGGSVPH (SEQ ID NO:41); AGGSVP (SEQ ID NO:42); AGGSV (SEQ ID NO:19); AGGS (SEQ ID NO:21).

The anti-IgE antibody described herein may bind to an epitope within the antigenic segment AAGGSVPHPRCH-CGAGRA (SEQ ID NO:1) that consists of any consecutive 4, 5, 6, 7, 8, 9, 10, 11, 12, 13 or 14 amino acids in SEQ ID NO:1.

An anti-IgE antibody may be an antibody that binds to the antigenic segment AAGGSVPHPRCHCGAGRA (SEQ ID NO:1) in a membrane-bound IgE (mIgE) molecule expressed on the surface of B cells and inhibits biological activity and/or downstream pathway(s) mediated by the mIgE. In some examples, an anti-IgE antibody provided herein suppresses mIgE-expressing B cell signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold.

In some embodiments, the anti-IgE antibody described herein can induce apoptosis and/or ADCC effects in B cells expressing mIgE, thereby effective in eliminating such B cells and treating IgE-mediated diseases such as allergic diseases. In some examples, the anti-IgE antibody described herein can eliminate at least 20%, at least 40%, at least 50%, at least 75%, at least 90%, or at least 95%, mIgE-expressing B cells in a subject (e.g., a human patient).

The binding affinity of an anti-IgE antibody to the antigenic segment AAGGSVPHPRCHCGAGRA (SEQ ID NO:1), or an antigenic epitope therein may be less than any of about 100 nM, about 50 nM, about 10 nM, about 1 nM, about 500 pM, about 100 pM, or about 50 pM to any of about 2 pM. Binding affinity may be expressed $K_D$ or dissociation constant, and an increased binding affinity corresponds to a decreased $K_D$. One way of determining binding affinity of antibodies to IgE is by measuring binding affinity of monofunctional Fab fragments of the antibody. To obtain monofunctional Fab fragments, an antibody (for example, IgG) may be cleaved with papain or expressed recombinantly. The affinity of an anti-IgE Fab fragment of an antibody may be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) may be obtained; and equilibrium dissociation constant ($K_D$) values may be calculated as $k_{off}/k_{on}$.

In some embodiments, the antibody binds the antigenic epitope AAGGSVPHPRCHCGAGRA (SEQ ID NO:1) of human IgE and does not significantly bind an IgE from another mammalian species. In some embodiments, the antibody binds a human IgE as well as at least one IgE from another mammalian species. The epitope(s) bound by the anti-IgE antibodies described herein may be continuous or discontinuous.

In some embodiments, the anti-IgE antibody described herein is anti-IgE antibody mAb 23B11, and its functional variants. The amino acid sequences of the heavy chain variable region ($V_H$) and light chain variable region ($V_L$) of mAb 23B11 are shown in FIG. 4. The complementarity determining regions of both the $V_H$ and $V_L$ chains are underlined in FIG. 4.

A functional variant (equivalent) of mAb 23B11 has essentially the same epitope-binding specificity as mAb 23B11 and exhibits at least 20% (e.g., 30%, 40%, 50%, 60%, 70%, 80%, 90%, or greater) of the activity of a signaling pathway mediated by mIgE as relative to mAb 23B11. In some embodiments, a functional variant of mAb 23B11 contains the same regions/residues responsible for antigen-binding as mAb 23B11, such as the same specificity-determining residues in the CDRs or the whole CDRs. The regions/residues responsible for antigen-binding may be identified from amino acid sequences of the heavy chain/light chain sequences of mAb 23B11 by methods known in the art. See, e.g., www.bioinf.org.uk/abs; Almagro, *J. Mol. Recognit.* 17:132-143 (2004); and Chothia et al., *J. Mol. Biol.* 227:799-817 (1987).

In some embodiments, a functional variant of mAb 23B11 comprises a $V_H$ chain that includes a $V_H$ CDR1, $V_H$ CDR2 and $V_H$ CDR3 at least 75% (e.g., 80%, 85%, 90%, 95%, or 98%) identical to the corresponding $V_H$ CDRs of mAb 23B11, and a $V_L$ chain that includes a $V_L$ CDR1, $V_L$ CDR2 and $V_L$ CDR3 at least 75% (e.g., 80%, 85%, 90%, 95%, or 98%) identical to the corresponding $V_H$ CDRs of mAb 23B11.

In some embodiments, a functional variant of mAb 23B11 comprises a $V_H$ chain at least 75% (e.g., 80%, 85%, 90%, 95%, or 98%) identical to the $V_H$ chain (mature or precursor) of mAb 23B11 and a $V_L$ chain at least 75% (e.g., 80%, 85%, 90%, 95%, or 98%) identical to the $V_L$ chain (mature of precursor) of mAb 23B11.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches may be performed with the XBLAST program, score=50, wordlength=3 to obtain amino acid sequences homologous to the protein molecules of interest. Where gaps exist between two sequences, Gapped BLAST may be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) may be used.

In some embodiments, a functional variant of mAb 23B11 comprises a $V_H$ chain that includes up to 5 (e.g., 1, 2, 3, 4, or 5) amino acid residue variations in the $V_H$ CDR regions ($V_H$ CDR1, CDR2 and/or CDR3) as compared to the $V_H$ CDRs of mAb 23B11, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_H$ CDRs of mAb 23B11.

In some embodiments, a functional variant of mAb 23B11 is a humanized antibody derived from mAb 23B11.

Antibody Preparation

Antibodies capable of binding the antigenic segment AAGGSVPHPRCHCGAGRA (SEQ ID NO:1), or an antigenic epitope therein (e.g., SEQ ID NO:4), of membrane-bound IgE on B lymphocytes (B cells) as described herein may be made by any method known in the art. See, e.g., Harlow and Lane, (1988) Antibodies: A Laboratory Manual, Cold Spring Harbor Laboratory, New York.

In some embodiments, the antibodies provided herein may be made by the conventional hybridoma technology. The full-length target antigen or a fragment thereof, optionally coupled to a carrier protein such as KLH, may be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom may be manipulated to serve as the basis for production of mammalian, including human hybridoma cell lines. A host animal may be inoculated intraperitoneally, intramuscularly, orally, subcutaneously, intraplantar, and/or intradermally with an amount of immunogen, including those described herein.

Hybridomas may be prepared from the lymphocytes and immortalized myeloma cells using the general somatic cell hybridization technique of Kohler, B. and Milstein, C. (1975) *Nature* 256:495-497 or as modified by Buck, D. W., et al., *In Vitro,* 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, may be used for culturing hybridomas that secrete monoclonal antibodies. As another alternative to the cell fusion technique, EBV immortalized B cells may be used to produce the anti-IgE monoclonal antibodies of the present disclosure. The hybridomas are expanded and subcloned, if desired, and supernatants are assayed for anti-immunogen activity by conventional immunoassay procedures (e.g., radioimmunoassay, enzyme immunoassay or fluorescence immunoassay).

Hybridomas that may be used as source of antibodies encompass all derivatives, progeny cells of the parent hybridomas that produce monoclonal antibodies capable of binding the antigenic segment AAGGSVPHPRCHCGAGRA (SEQ ID NO:1), or an antigenic epitope therein, of membrane-bound IgE (mIgE) on human B lymphocytes (B cells). Hybridomas that produce such antibodies may be grown in vitro or in vivo using known procedures. The monoclonal antibodies may be isolated from culture media or body fluids, by conventional immunoglobulin purification procedures such as, for example, ammonium sulfate precipitation, gel electrophoresis, dialysis, chromatography and/or ultrafiltration. Undesired activity if present, may be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, for example, keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R₁N=C=NR, where R and R₁ are different alkyl groups, can yield a population of antibodies (e.g., monoclonal antibodies).

In some embodiments, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the antigenic segment AAGGSVPHPRCHCGAGRA (SEQ ID NO:1), or an antigenic epitope therein. It will be apparent to one of skill in the art that at least one polynucleotide change may be made to the antibody and still maintain its binding specificity to the target antigen.

In other embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) may be used to produce human antibodies and antibody fragments in vitro, from immunoglobulin variable (V) domain gene repertoires from unimmunized donors.

Antigen-binding fragments of an intact antibody (full-length antibody) may be prepared via routine methods. For example, $F(ab')_2$ fragments may be produced by pepsin digestion of an antibody molecule, and Fab fragments may be generated by reducing the disulfide bridges of $F(ab')_2$ fragments.

Genetically engineered antibodies, such as humanized antibodies, chimeric antibodies, single-chain antibodies, and bi-specific antibodies, may be produced through, for example, conventional recombinant technology. In some embodiments, DNA encoding a monoclonal antibodies specific to a target antigen may be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA may then be modified, for example, by substituting the coding sequence for human heavy and light chain constant domains in place of the homologous murine sequences, Morrison et al., (1984) *Proc. Nat. Acad. Sci.* 81:6851, or by covalently joining to the immunoglobulin coding sequence all or part of the coding sequence for a non-immunoglobulin polypeptide. In that manner, genetically engineered antibodies, such as "chimeric" or "hybrid" antibodies, may be prepared that have the binding specificity of a target antigen.

Techniques developed for the production of "chimeric antibodies" are well known in the art. See, e.g., Morrison et al. (1984) *Proc. Natl. Acad. Sci. USA* 81, 6851; Neuberger et al. (1984) *Nature* 312, 604; and Takeda et al. (1984) *Nature* 314:452.

Methods for constructing humanized antibodies are also well known in the art. See, e.g., Queen et al. (1989) *Proc. Natl. Acad. Sci. USA,* 86:10029-10033. In some embodiments, variable regions of $V_H$ and $V_L$ of a parent non-human antibody may be subjected to three-dimensional molecular modeling analysis following methods known in the art. Next, framework amino acid residues predicted to be important for the formation of the correct CDR structures may be identified using the same molecular modeling analysis. In parallel, human $V_H$ and $V_L$ chains having amino acid sequences that are homologous to those of the parent non-human antibody may be identified from any antibody gene database using the parent $V_H$ and $V_L$ sequences as search queries. Human $V_H$ and $V_L$ acceptor genes may then selected.

The CDR regions within the selected human acceptor genes may be replaced with the CDR regions from the parent non-human antibody or functional variants thereof. In some embodiments, residues within the framework regions of the parent chain that are predicted to be important in interacting with the CDR regions (see above description) may be used to substitute for the corresponding residues in the human acceptor genes.

A single-chain antibody may be prepared using recombinant technology by linking a nucleotide sequence coding for a heavy chain variable region and a nucleotide sequence coding for a light chain variable region. A flexible linker may be incorporated between the two variable regions. Alternatively, techniques described for the production of single chain antibodies (U.S. Pat. Nos. 4,946,778 and 4,704,692) may be adapted to produce a phage scFv library and scFv clones specific to IgE may be identified from the library following routine procedures. Positive clones may be subjected to further screening to identify those antibodies that bind the antigenic segment AAGGSVPHPRCHCGAGRA (SEQ ID NO:1), or an antigenic epitope therein, of IgE.

Antibodies obtained following a method known in the art and described herein may be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping may be used to determine the sequence to which an antibody binds. A linear epitope refers to an epitope contained in a single stretch of amino acids. A conformational epitope refers to an epitope formed by a three-dimensional interaction of amino acids that may not necessarily be contained in a single stretch (primary structure linear sequence). Peptides of varying lengths (e.g., at least 4-6 amino acids long) may be isolated or synthesized (e.g., recombinantly) and used for binding assays with an antibody. In some embodiments, the epitope to which the antibody binds may be determined in a systematic screening by using overlapping peptides derived from the target antigen sequence and determining binding by the antibody. According to gene fragment expression assays, the open reading frame encoding the target antigen may be fragmented either randomly or by specific genetic constructions and the reactivity of the expressed fragments of the antigen with the antibody to be tested may be determined. Gene fragments may, for example, be produced by PCR and then transcribed and translated into protein in vitro, in the presence of radioactive amino acids. The binding of the antibody to the radioactively labeled antigen fragments may then determined by immunoprecipitation and gel electrophoresis. Certain epitopes may also be identified by using large libraries of random peptide sequences displayed on the surface of phage particles (phage libraries). In some embodiments, a defined library of overlapping peptide fragments may be tested for binding to the test antibody in simple binding assays. In some embodiments, mutagenesis of an antigen-binding domain, domain swapping experiments and alanine scanning mutagenesis may be performed to identify residues required, sufficient, and/or necessary for epitope binding. For example, domain swapping experiments may be performed using a mutant of a target antigen in which various fragments of the antigenic segment AAGGSVPHPRCHCGAGRA (SEQ ID NO:1) have been replaced (swapped) with sequences from a closely related, but antigenically distinct protein (such as another member of the neurotrophin protein family). By assessing binding of the antibody to the mutant linear epitope, the importance of the particular antigen fragment to antibody binding may be assessed.

In some embodiments, competition assays may be performed using other antibodies known to bind to the same antigen to determine whether an antibody binds to the same epitope as the other antibodies. Competition assays are well known to those of skill in the art.

In some embodiments, any of the anti-IgE antibodies described herein, such as mAb 23B11 and its functional variants, can be prepared via recombinant technology. For examples, nucleic acids comprising nucleotide sequences encoding the heavy and light chain variable regions of such an antibody can be cloned into expression vectors (e.g., a bacterial vector such as an *E. coli* vector, a yeast vector, a viral vector, or a mammalian vector) via routine technology. See, e.g., Sambrook et al., Molecular Cloning, A Laboratory Manual, 3rd Ed., Cold Spring Harbor Laboratory Press. For example, the nucleic acids and vectors can be contacted, under suitable conditions, with a restriction enzyme to create complementary ends on each molecule that can pair with each other and be joined together with a ligase. Alternatively, synthetic nucleic acid linkers can be ligated to the termini of a coding sequence. These synthetic linkers contain nucleic acid sequences that correspond to a particular restriction site in the vector. Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Suitable vectors and methods for producing vectors containing transgenes are well known and available in the art. See, e g., Sambrook et al., Molecular Cloning, A Laboratory Manual, 3rd Ed., Cold Spring Harbor Laboratory Press.

In some examples, the nucleotide sequences encoding the heavy and light chain variable regions are inserted into the same expression vector and are in operably linkage with a suitable promoter. The coding sequences of both the heavy chain and light chain variable regions can be in operable linkage to the same suitable promoter. In this case, an internal ribosomeal entry site (IRES) can be inserted between the two coding sequences. Alternatively, each coding sequence can be in operable linkage to a distinct promoter. In other examples the nucleotide sequences encoding the heavy and light chain variable regions are inserted into two different expression vectors, each being operably linked to a suitable promoter.

A variety of promoters can be used for expression of the anti-IgE antibodies described herein. Promoters that can be used to express the protein are well known in the art. Promoters include cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter [F. Yao et al., Human Gene Therapy, supra]. One particular advantage of this tetracycline inducible switch is that it does not require the use of a tetracycline repressor-mammalian cells transactivator or repressor fusion protein, which in some instances can be toxic to cells [M. Gossen et al., Natl. Acad. Sci. USA, 89:5547-5551 (1992); P. Shockett et al., Proc. Natl. Acad. Sci. USA, 92:6522-6526 (1995)], to achieve its regulatable effects.

Examples of polyadenylation signals useful to practice the methods described herein include, but are not limited to, human collagen I polyadenylation signal, human collagen II polyadenylation signal, and SV40 polyadenylation signal.

Selectable markers can be used to monitor uptake of the desired transgene into the progenitor cells described herein. These marker genes can be under the control of any promoter or an inducible promoter. These are known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, and LacZ.

Any of the vectors described herein can be introduced into a suitable host cells (e.g., bacterial cells, yeast cells, plant cells, or mammalian cells) for expression of the antibodies. Such host cells can be cultured in a suitable medium under conditions allowing for the expression of the antibodies, which can be purified from either the cultured cells or from the culture medium. The antibody heavy and light chains of the antibodies, if produced separately, can be incubated under suitable conditions for antibody assembly.

Any of the nucleic acids encoding the heavy and light chain variable regions, vectors (e.g., expression vectors) comprising such, and host cells comprising the vectors, as well as methods for producing the antibodies as described herein are also within the scope of the present disclosure.
Compositions and Pharmaceutical Compositions Any of the anti-IgE antibodies provided herein, or the encoding nucleic acids thereof, may be mixed with a pharmaceutically acceptable carrier (excipient), including buffer, to form a pharmaceutical composition for use in treating. "Acceptable" means that the carrier must be compatible with the active ingredient of the composition (and preferably, capable of stabilizing the active ingredient) and not deleterious to the subject to be treated. Pharmaceutically acceptable excipients (carriers) include buffers, which are well known in the art. See, e.g., Remington: The Science and Practice of Pharmacy 20th Ed. (2000) Lippincott Williams and Wilkins, Ed. K. E. Hoover. In some embodiments, a pharmaceutical composition described herein contains more than one anti-IgE antibody that recognizes different epitopes or fragments of the linear peptide AAGGSVPHPRCHCGAGRA (SEQ ID NO:1).

The pharmaceutical compositions to be used in the present methods may comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing antibodies that bind the antigenic segment AAGGSVPHPRCHCGAGRA (SEQ ID NO:1), or an antigenic epitope therein, of IgE, which may be prepared by methods known in the art, such as described in Epstein, et al., *Proc. Natl. Acad. Sci. USA* 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. In some embodiments, liposomes may be generated by the reverse phase evaporation method with a lipid composition comprising phosphatidylcholine, cholesterol and PEG-derivatized phosphatidylethanolamine (PEG-PE). Liposomes may be extruded through filters of defined pore size to yield liposomes with the desired diameter.

Antibodies that bind the antigenic segment AAGGSVPHPRCHCGAGRA (SEQ ID NO:1), or an antigenic epitope therein, of IgE may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein may be formulated in sustained-release format. Suitable examples of sustained-release preparations include semipermeable matrices of solid hydrophobic polymers containing the antibody, which matrices are in the form of shaped articles, for example, films, or microcapsules. Examples of sustained-release matrices for use as described herein include, without limitation, polyesters, hydrogels (for example, poly(2-hydroxyethyl-methacrylate), or polyvinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration are typically sterile. This may be accomplished by, for example, by filtration through sterile filtration membranes. In some embodiments, therapeutic antibody compositions may be placed into a container having a sterile access port, for example, an intravenous solution bag or vial having a stopper pierceable by a hypodermic injection needle.

The pharmaceutical compositions described herein may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the antibodies that bind the antigenic segment AAGGSVPHPRCHCGAGRA (SEQ ID NO:1), or an antigenic epitope therein, of IgE may be mixed with a pharmaceutical carrier such as, for example, a conventional tableting ingredient such as corn starch, lactose, sucrose, sorbitol, talc, stearic acid, magnesium stearate, dicalcium phosphate or gums. The anti-IgE antibodies of the present disclosure may also be mixed with other pharmaceutical diluents such as, for example, water to form a solid pre-formulation composition containing a homogeneous mixture of the antibodies. When referring to these pre-formulation compositions as homogeneous, it is meant that the antibodies are dispersed evenly throughout the composition so that the composition may be readily subdivided into equally effective unit dosage forms such as tablets, pills and capsules. This solid pre-formulation composition may then be subdivided into unit dosage forms of the type described above containing from 0.1 to about 500 mg of the active ingredient of the present invention. The tablets or pills of the compositions provided herein may be coated or otherwise compounded to provide a dosage form affording the advantage of prolonged action. For example, the tablet or pill may comprise an inner dosage and an outer dosage component, the latter being in the form of an envelope over the former. The two components may be separated by an enteric layer that serves to resist disintegration in the stomach and permits the inner component to pass intact into the duodenum or to be delayed in release. A variety of materials may be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g. Span™ 20, 40, 60, 80 or 85), any of which may be used in the composition and methods described herein. Compositions with a surface-active agent may comprise, in some embodiments, between 0.05 and 5% surface-active agent, and may be between 0.1 and 2.5%. It will be appreciated that other ingredients may be added including, without limitation, mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil and/or almond oil) and an emulsion formed upon mixing with a phospholipid (e.g., egg phospholipids, soybean phospholipids or soybean lecithin) and water. It will be appreciated that other ingredients may be added including, without limitation, glycerol or glucose, to adjust the tonicity of the emulsion. Suitable emulsions may contain up to 20% oil, for example, between 5 and 20%. The fat emulsion may comprise fat droplets between 0.1 and 1.0 .im, particularly 0.1 and 0.5 .im, and may have a pH in the range of 5.5 to 8.0.

The emulsion compositions may be those prepared by mixing anti-IgE antibodies with Intralipid™ or the components thereof (soybean oil, egg phospholipids, glycerol and water).

Pharmaceutical compositions for inhalation or insufflation include, without limitation, solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Use of Anti-IgE Antibodies or Encoding Nucleic Acids for Treating IgE-Mediated Conditions The antibodies that bind the antigenic segment AAGGS-VPHPRCHCGAGRA (SEQ ID NO:1), or an antigenic epitope therein, of IgE (e.g., mAb 23B11 or a function variant thereof) may be used to treat an IgE-mediated condition. Examples of IgE mediated conditions that may be treated using the antibodies (or compositions) provided herein include, without limitation, atopic disorders, which are characterized by a general inherited propensity to respond immunologically to many common naturally occurring inhaled and ingested antigens and the continual production of IgE antibodies. Specific atopic disorders include allergic asthma, allergic rhinitis (conjunctivitis), atopic dermatitis, food allergy, anaphylaxis, contact dermatitis, allergic gastroenteropathy, allergic bronchopulmonary aspergillosis and allergic purpura (Henoch-Schönlein). Atopic patients often have multiple allergies, meaning that they have IgE antibodies to, and symptoms from, many environmental allergens, including seasonal, perennial and occupational allergens. Examples of seasonal allergens include pollens (e.g., grass, tree, rye, timothy, ragweed), while examples of perennial allergens include fungi (e.g., molds, mold spores), feathers, animal (e.g., pet or other animal dander) and insect (e.g., dust mite) debris. Examples of occupational allergens also include animal (e.g. mice) antigens and plant antigens as well as drugs, detergents, metals and immunoenhancers such as isocyanates. Non-antigen specific stimuli that can result in an IgE-mediated reaction include infection, irritants such as smoke, combustion fumes, diesel exhaust particles and sulphur dioxide, exercise, cold and emotional stress. Specific hypersensitivity reactions in atopic and nonatopic individuals with a certain genetic background may result from exposure to proteins in foods (e.g., legumes, peanuts), venom (e.g., insect, snake), vaccines, hormones, antiserum, enzymes, latex, antibiotics, muscle relaxants, vitamins, cytotoxins, opiates, and polysaccharides such as dextrin, iron dextran and polygeline.

Other conditions associated with elevated IgE levels, that appear to be IgE-mediated and are treatable with the antibodies and composition of the present disclosure include, without limitation, ataxia-telangiectasia, Churg-Strauss Syndrome, eczema, enteritis, gastroenteropathy, graft-versus-host reaction, hyper-IgE (Job's) syndrome, hypersensitivity (e.g., anaphylactic hypersensitivity, candidiasis, vasculitis), IgE myeloma, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis, parasitic diseases (e.g., trypanosomiasis), hypersensitivity vasculitis, urticaria and Wiskott-Aldrich syndrome.

Further, conditions that may be treated by lowering IgE levels, regardless of whether the conditiosn themselves are associated with elevated IgE and thus should be considered within the scope of "IgE-mediated condition," include, without limitation, Addison's disease (chronic adrenocortical insufficiency), alopecia, hereditary angioedema, anigioedema (Bannister's disease, angioneurotic edema), ankylosing spondylitis, aplastic anemia, arteritis, amyloidosis, immune disorders, such as autoimmune hemolytic anemia, autoimmune oophoritis, autoimmune orchitis, autoimmune polyendocrine failure, autoimmune hemolytic anemia, autoimmunocytopenia, autoimmune glomerulonephritis, Behcet's disease, bronchitis, Buerger's disease, bullous pemphigoid, Caplan's syndrome (rheumatoid pneumoconiosis), carditis, celiac sprue, Chediak-Higashi syndrome, chronic obstructive lung Disease (COPD), Cogan-Reese syndrome (iridocorneal endothelial syndrome), CREST syndrome, dermatitis herpetiformis (Duhring's disease), diabetes mellitus, eosinophilic fasciitis, eosinophilic nephritis, episcleritis, extrinsic allergic alveolitis, familial paroxysmal polyserositis, Felty's syndrome, fibrosing alveolitis, glomerulonephritis, Goodpasture's syndrome, granulocytopenia, granuloma, granulomatosis, granuloma myositis, Graves' disease, Guillain-Barre syndrome (polyneuritis), Hashimoto's thyroiditis (lymphadenoid goiter), hemochromatosis, histiocytosis, hypereosinophilic syndrome, irritable bowel syndrome, juvenile arthritis, keratitis, leprosy, lupus erythematosus, Lyell's disease, Lyme disease, mixed connective tissue disease, mononeuritis, mononeuritis multiplex, Muckle-Wells syndrome, mucocutaneous lymphoid syndrome (Kawasaki's disease), multicentric reticulohistiocystosis, multiple sclerosis, myasthenia gravis, mycosis fungoides, panninculitis, pemphigoid, pemphigus, pericarditis, polyneuritis, polyarteritis nodoas, psoriasis, psoriatic arthritis, pulmonary arthritis, pulmonary adenomatosis, pulmonary fibrosis, relapsing polychondritis, rheumatic fever, rheumatoid arthritis, rhinosinusitis (sinusitis), sarcoidosis, scleritis, sclerosing cholangitis, serum sickness, Sezary syndrome, Sjögren's syndrome, Stevens-Johnson syndrome, systemic mastocytosis, transplant rejection, thrombocytopenic purpura, thymic alymphoplasia, uveitis, vitiligo and Wegener's granulomatosis.

Autoimmune conditions associated with elevated IgE levels that appear to be IgE-mediated may be treated with the antibodies and composition of the present disclosure. An "autoimmune condition" herein is a disease or disorder arising from and directed against an individual's own tissues or organs or a co-segregation or manifestation thereof or resulting condition therefrom. In many autoimmune and inflammatory conditions, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to any one theory regarding B-cell mediated autoimmune conditiosn, it is believed that B cells demonstrate a pathogenic effect in human autoimmune conditions through many mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune conditions.

"Autoimmune conditions" may also include an organ-specific condition (e.g., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system and/or a systemic condition that can affect multiple organ systems (for example, systemic lupus erythematosus (SLE), rheumatoid arthritis (RA) and polymyositis). Such conditions include autoimmune rheumatologic disorders (such as, for example, RA, Sjögren's syndrome, scleroderma, lupus such as SLE and lupus nephritis, polymyositis-dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, celiac disease, vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)).

To practice the method disclosed herein, an effective amount of the pharmaceutical composition described above may be administered to a subject (e.g., a human) in need of the treatment through a suitable route, such as intravenous administration, for example, as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers may be used for administration. Liquid formulations may be directly nebulized and lyophilized powder may be nebulized after reconstitution. In some embodiments, anti-IgE antibodies may be aerosolized using a fluorocarbon formulation and a metered dose inhaler, or inhaled as a lyophilized and milled powder.

The subject to be treated by the methods described herein may be a mammal such as, for example, a human. Mammals include, without limitation, humans, farm animals, sport animals, pets, primates, horses, dogs, cats, mice and rats. A human subject who is in need of treatment of may be a human patient having, at risk for, or suspected of having an IgE-mediated condition (e.g., allergic asthma, allergic rhinitis, or atopic dermatitis). A subject having an IgE-mediated condition may be identified by routine medical examination, for example, by laboratory tests, allergy tests and/or mucosal swabs. A subject suspected of having an IgE-mediated condition might show one or more symptoms of the condition, which may involve the gastrointestinal tract, skin, or respiratory tract, and which may include stuffy nose, hives, rash and/or anaphylactic shock. A subject at risk for an IgE-mediated condition may be a subject having one or more risk factors for that disorder, which include host and environmental factors. For example, risk factors associated with IgE-mediated conditions include family history/heredity, age (children may be at higher risk than adults), gender, race, exposure to infectious disease during early childhood, environmental pollution, allergen levels and diet (e.g., dietary changes).

"An effective amount" as used herein refers to the amount of each active agent (e.g., anti-IgE antibodies) required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and may be addressed with no more than routine experimentation. In some embodiments, a maximum dose of the individual components or combinations thereof may be used, that is, the highest safe dose according to sound medical judgment. It will be understood by those of ordinary skill in the art that a patient may insist upon a lower dose or tolerable dose for medical reasons, psychological reasons or for virtually any other reason.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of an IgE-mediated condition. Alternatively, sustained continuous release formulations of anti-IgE antibodies may be appropriate. Various formulations and devices for achieving sustained release are known in the art.

In some embodiments, dosages for anti-IgE antibodies as described herein may be determined empirically in individuals who have been given one or more administration(s) of anti-IgE antibodies. Individuals are given incremental dosages of the antibodies. To assess efficacy of the antibodies, an indicator of an IgE-mediated condition may be followed.

Generally, for administration of any of the antibodies described herein, an initial candidate dosage may be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the IgE-mediated condition, the treatment may be sustained until a desired suppression of symptoms occurs or until sufficient therapeutic levels are achieved to alleviate the condition, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency may be once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) may vary over time.

For the purpose of the present disclosure, the appropriate dosage of anti-IgE antibodies will depend on the specific antibody (or compositions thereof) employed, the type and severity of the IgE-mediated condition, whether the antibodies are administered for preventive or therapeutic purposes, previous therapy, the patient's clinical history and response to the antibodies, and the discretion of the attending physician. Typically the clinician will administer anti-IgE antibodies (e.g., antibodies that bind antigenic segment AAGGSVPHPRCHCGAGRA (SEQ ID NO:1), or an antigenic epitope therein, of IgE) until a dosage is reached that achieves the desired result. Administration of anti-IgE antibodies may be continuous or intermittent, depending, for example, upon the recipient's physiological condition, whether the purpose of the administration is therapeutic or prophylactic, and other factors known to skilled practitioners. The administration of anti-IgE antibodies may be essentially continuous over a preselected period of time or may be in a series of spaced dose, for example, either before, during, or after developing an IgE-mediated condition.

As used herein, the term "treating" refers to the application or administration of a composition including one or more anti-IgE antibodies to a subject, who has an IgE-mediated condition, a symptom of an IgE-mediated condition, or a predisposition toward the condition, with the purpose to cure, heal, alleviate, relieve, alter, remedy, ameliorate, improve, or affect the condition, the symptom of the condition, or the predisposition toward the condition.

Alleviating an IgE-mediated condition includes delaying the development or progression of the condition, or reducing condition severity. Alleviating the condition does not necessarily require curative results. As used therein, "delaying" the development of a condition (such as an IgE-mediated condition) means to defer, hinder, slow, retard, stabilize, and/or postpone progression of the condition. This delay may be of varying lengths of time, depending on the history of the condition and/or individuals being treated. A method that "delays" or alleviates the development of a condition, or delays the onset of the condition, is a method that reduces probability of developing one or more symptoms of the condition in a given time frame and/or reduces extent of the symptoms in a given time frame, when compared to not using the method. Such comparisons are typically based on clinical studies, using a number of subjects sufficient to give a statistically significant result.

"Development" or "progression" of a condition means initial manifestations and/or ensuing progression of the disease. Development of the condition may be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of an IgE-mediated condition includes initial onset and/or recurrence.

In some embodiments, the anti-IgE antibodies described herein are administered to a subject in need of the treatment at an amount sufficient to reduce the level of the IgE-mediated signaling by at least 20% (e.g., 30%, 40%, 50%, 60%, 70%, 80%, 90% or greater). In some embodiments, the antibodies are administered in an amount effective to mediate apoptosis of mIgE-expressing B transfectoma cells.

Conventional methods, known to those of ordinary skill in the art of medicine, may be used to administer the antibodies or a pharmaceutical composition containing the antibodies to the subject, depending upon the type of disease to be treated or the site of the disease. This composition may also be administered through other conventional routes including, without limitation, being administered orally, parenterally, by inhalation spray, topically, rectally, nasally, buccally, vaginally or by an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, antibodies or a pharmaceutical composition containing the antibodies may be administered to the subject through injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies may be administered by the drip method, whereby a pharmaceutical formulation containing the antibodies and a physiologically acceptable excipients is infused. Physiologically acceptable excipients may include, without limitation, 5% dextrose, 0.9% saline, Ringer's solution and other suitable excipients. Intramuscular preparations such as, for example, sterile formulations of a suitable soluble salt form of the antibodies, may be dissolved and administered in a pharmaceutical excipient such as Water-for-Injection, 0.9% saline, or 5% glucose solution.

In some embodiments, anti-IgE antibodies are administered through site-specific or targeted local delivery techniques. Examples of site-specific or targeted local delivery techniques include various implantable depot sources of the anti-IgE antibodies or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

The particular dosage regimen (e.g., dose, timing and repetition) used in the method described herein will depend on the particular subject and that subject's medical history.

Treatment efficacy may be assessed by methods well-known in the art.

Also provided herein are compositions comprising nucleic acids encoding any of the anti-IgE antibodies of the present disclosure.

Immunopeptides and Immune Compositions Comprising Such

Also described herein are immunogenic peptides derived from the antigenic segment of CεmX described herein. The term "peptide" means a compound in which amino acids are bonded to each other by peptide bond. Preferably, the peptide contains up to 200 amino acid residues, e.g., up to 150 aa, 100 aa, 80 aa, 50 aa, or 25 aa. Alternatively, the peptide can have a molecular weight of about 15-20 kD, or less.

The immunogenic peptide described here can be SEQ ID NO:1 or a fragment thereof (containing at least 4 (e.g., 5, 6, 7, 8, 9, 10, or more) consecutive amino acid residues in SEQ ID NO:1). In some embodiments, the immunogenic peptide can be the peptide of SEQ ID NO:3 or SEQ ID NO:4. In some examples, such immunogenic peptide can be linked to a heterologous sequence at the N-terminus, the C-terminus, or both. A heterologous sequence may be derived from a non-IgE protein or derived from a domain of an IgE protein other than the CεmX domain. When necessary, the heterologous sequence can be derived from a region within the CεmX domain not adjacent to the immunogenic peptide.

When necessary, the immunogenic peptide described herein can further comprise another segment that is heterologous to the CεmX segment. For example, the other segment is derived from a non-mIgE protein or from a region of an mIgE not consecutive to the first and second segments. In some examples, the immunogenic peptide may be conjugated to a carrier to enhance its immunogenicity. Suitable carriers include, but are not limited to, viral-like particles (VLPs), poly(lactic-co-glycolic) acid (PLGA) microparticles, CpG oligodeoxynucleotide, and liposome.

The immunogenic peptides described herein can be prepared by a conventional method, e.g., chemical synthesis or recombinant technology. The peptides may first require chemical modification to improve their half-life in vivo. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

The immunogenic peptide can be used to form immunogenic compositions (e.g., vaccine) for use in eliciting immune responses specific to the CεmX segment, e.g., antibody responses. Methods for preparing immunogenic compositions are well known in the art, e.g., those described above.

For example, methods for preparing vaccines are generally well known in the art, as exemplified by U.S. Pat. Nos. 4,601,903; 4,599,231; 4,599,230; and 4,596,792. Vaccines may be prepared as injectables, as liquid solutions or emulsions. The immunogenic peptide of this disclosure may be mixed with physiologically acceptable and excipients compatible. Excipients may include, water, saline, dextrose, glycerol, ethanol, and combinations thereof. The vaccine may further contain minor amounts of auxiliary substances such as wetting or emulsifying agents, pH buffering agents, or an adjuvant to enhance the effectiveness of the vaccines. Methods of achieving adjuvant effect for the vaccine include use of agents, such as aluminum hydroxide or phosphate (alum), commonly used as 0.05 to 0.1 percent solutions in phosphate buffered saline. Vaccines may be administered parenterally, by injection subcutaneously or intramuscularly. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10-95% of the immunogenic peptide described herein.

Kits for Use in Alleviating IgE-Mediated Conditions

The present disclosure also provides kits for use in alleviating IgE-mediated conditions. Such kits may include one or more containers comprising anti-IgE antibodies (e.g., antibodies that bind the antigenic segment AAGGSVPHPRCHCGAGRA (SEQ ID NO:1), or an antigenic epitope therein, of IgE such as, for example, mAb 23B11 or its functional variant). Alternatively or in addition, such a kit can include one or more of the immunogenetic peptides or immune compositions described herein, e.g., AAGGSVPHPRCHCGAGRA (SEQ ID NO:1) or an immunogenic epitope thereof.

In some embodiments, the kit may comprise instructions, or directions for obtaining instructions, for use in accordance with any of the methods described herein. The included instructions may comprise a description of administration of the anti-IgE antibodies or the immunogenic peptides to treat, delay the onset, or alleviate IgE-mediated conditions according to any of the methods described herein. The kit may further comprise a description of selecting an individual suitable for treatment based on identifying whether that individual has an IgE-mediated condition. In some embodiments, the instructions comprise a description of administering anti-IgE antibodies to an individual at risk of an IgE-mediated condition.

The instructions relating to the use of anti-IgE antibodies generally include information as to dosage, dosing schedule, and route of administration for the intended treatment. The containers may be unit doses, bulk packages (e.g., multi-dose packages) or sub-unit doses. Instructions supplied in the kits of the present disclosure may be written instructions on a label or package insert (e.g., a paper sheet included in the kit). Machine-readable instructions (e.g., instructions carried on a magnetic or optical storage disk, or available via the World Wide Web) are also acceptable.

The label or package insert may indicated that the composition is used for treating, delaying the onset and/or alleviating an IgE-mediated conditions. Instructions may be provided for practicing any of the methods described herein.

The kits of the present disclosure may be in suitable packaging. Suitable packaging includes, without limitation, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (e.g., the container may be an intravenous solution bag or a vial having a stopper pierceable by a hypodermic injection needle). The container may also have a sterile access. At least one active agent in the composition is an antibody that binds the antigenic segment AAGGSVPHPRCHCGAGRA (SEQ ID NO:1) or an antigenic epitope therein, of IgE (e.g., mAb 23B11 or a functional variant thereof), or any of the immunogenic peptides as described herein.

Kits may optionally provide additional components such as buffers and interpretive information. In some embodiments, the kit comprises a container and a label or package insert(s) on or associated with the container. In some embodiments, the present disclosure provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Preparation of Anti-IgE Monoclonal Antibody mAb 23B11

A synthetic 22 amino acid peptide, GLPRAAGGSVPHPRCHCGAGRA (referred to as P(25→46) (SEQ ID NO:43), corresponding to amino acids 25-46 of CεmX and containing the junction of Peptide M1'-8 and A20 peptide, was conjugated to ovalbumin (OVA) and used for immunizing BALB/c mice.

Female BALB/c mice, 6-8 weeks old, were immunized three times subcutaneously at 2-wk intervals with P(25→46)-OVA using TiterMax® Gold as an adjuvant. A final boost was administered by intraperitoneal injection with 100 μg of P(25→46)-OVA in the absence of adjuvant. Three days later, the spleen cells from immunized mice were used for generating hybridoma clones.

To screen hybridomas for antibody secretion and to map the epitopes of secreted antibodies, the wells of microtiter plates were coated by incubating them overnight at 4° C. with 10 μg/mL of P(25→46) in 0.1 M carbonate buffer, pH 9.6. The wells were first blocked for 1 hour with 1% bovine serum albumin (BSA) in phosphate buffered saline (PBS), pH7.3, and then incubated for 1 hour at 37° C. at various dilutions with antisera or control antibodies. The wells were then washed and the ligand-bound antibodies detected by horse radish peroxidase (HRP)-conjugated goat anti-mouse IgG, Fcγ fragment specific (Jackson ImmunoResearch), or anti-human IgG, Fcγ fragment specific (Jackson ImmunoResearch) at a dilution of 1:10,000. To detect the ligand-bound antibodies, the wells were incubated for 1 hour at 37° C., followed by incubation with TMB (3,3',5,5'-tetramethylbenzidine) substrate (Clinical Scientific Products). The optical density (OD) was determined at 450 nm and revealed antibodies specific for an epitope within P(25→46).

One exemplary anti-IgE clone, mAb 23B11, was identified as capable of binding to the target antigen peptide. The $V_H$ and $V_L$ gene segments of mAb 23B11 were PCR-amplified from the hybridoma clone secreting mAb 23B11 and sequenced. The derived amino acid sequences of the $V_H$ and $V_L$ of mAb 23B11 are shown in FIG. 4. The complementarity determining regions (CDRs) of both the $V_H$ and $V_L$ chains are underlined.

Example 2: Epitope Mapping of mAb 23B11

One of the monoclonal antibodies specific for an epitope within the P(25→46), herein designated mAb 23B11, was subjected to epitope mapping studies. Several peptides representing parts of the consecutive P(25→46) were synthesized, including P(29→46) (SEQ ID NO:1); P(31→46) (SEQ ID NO:3), P(33→46) (SEQ ID NO:4), P(27→40) (SEQ ID NO:5), and P(23→37) (SEQ ID NO:6), as shown in FIG. 1A. P(27→40) is also referred to herein as Peptide M1'-8. The reactivity of mAb 23B11 with the synthesized peptides were analyzed by ELISA. The results from the ELISA are shown in FIG. 1, panel B. The mAbs 26A11, 26H2 and a20 were included for comparison.

The results in FIG. 1 show that the removal of the N-terminal AAGG (SEQ ID NO:44) from P(29→46) peptide does not affect binding by mAb 23B11, which suggests that the binding of mAb 23B11 to P(27→40) (i.e., Peptide M1'-8) is to its C-terminal part. These data are consistent that mAb 23B11 maintains maximal binding to P(33→46). The data together indicate that the antigenic epitope is SVPHPRCHCGAGRA (SEQ ID NO:1), amino acids 33-46 of M1' Peptide. The mAbs 26A11, 26H2, and a20, which bind to epitopes adjacent to SVPHPRCHCGAGRA (SEQ ID NO:4), do not recognize this epitope. Thus, SVPHPRCHCGAGRA (SEQ ID NO:4) represents a discrete new antigenic epitope.

Example 3: The Binding of mAb 23B11 to mIgE-Expressing Ramos Transfectants

Figure 2:
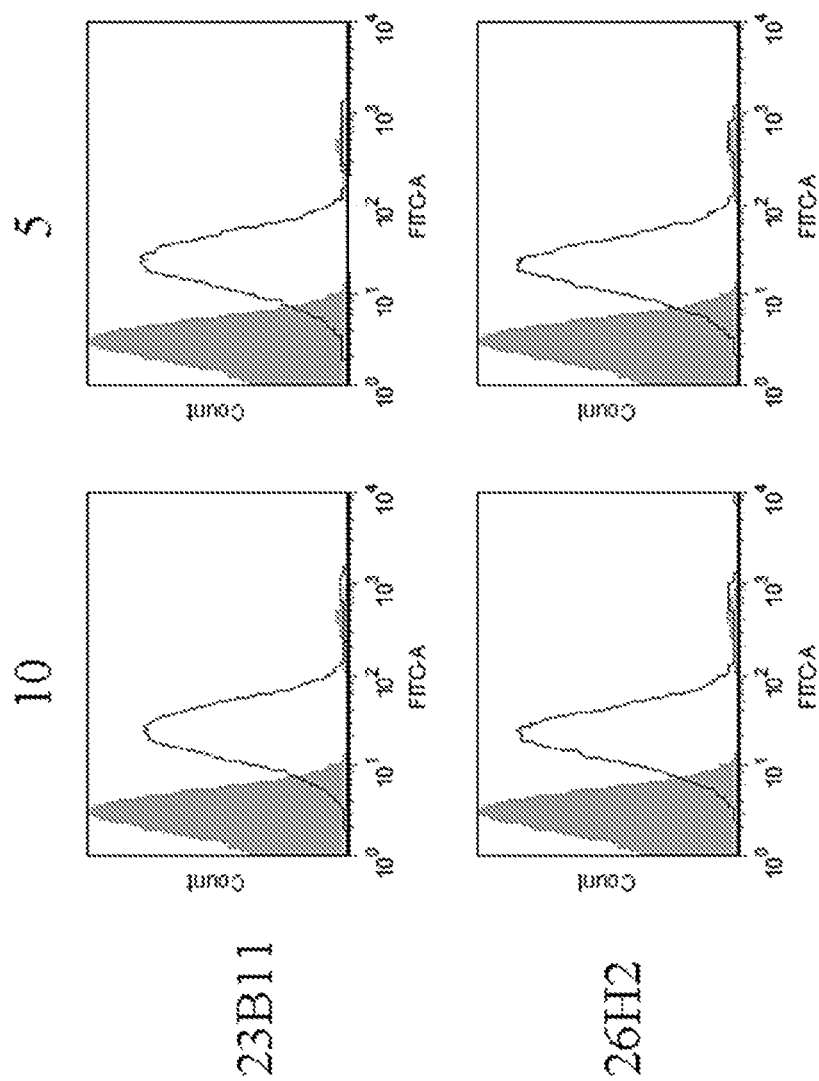
FIG. 2 is a graphs representing the binding affinity of mAb 23B11 to Ramos lines that express mIgE.Fc$_L$ (line profiles). The binding of mAb 23B11 to cells expressing mIgE.Fc$_S$ (shaded histograms) is shown as background. Ramos cells were incubated with 10, 5, 2.5, 1.25 and 0.625 µg/ml of mAb 23B11 or mAb 26H2 (as a control) on ice for 20 min, followed by staining with FITC-labeled rabbit F(ab')$_2$ specific for mouse IgG.
Figure 2:
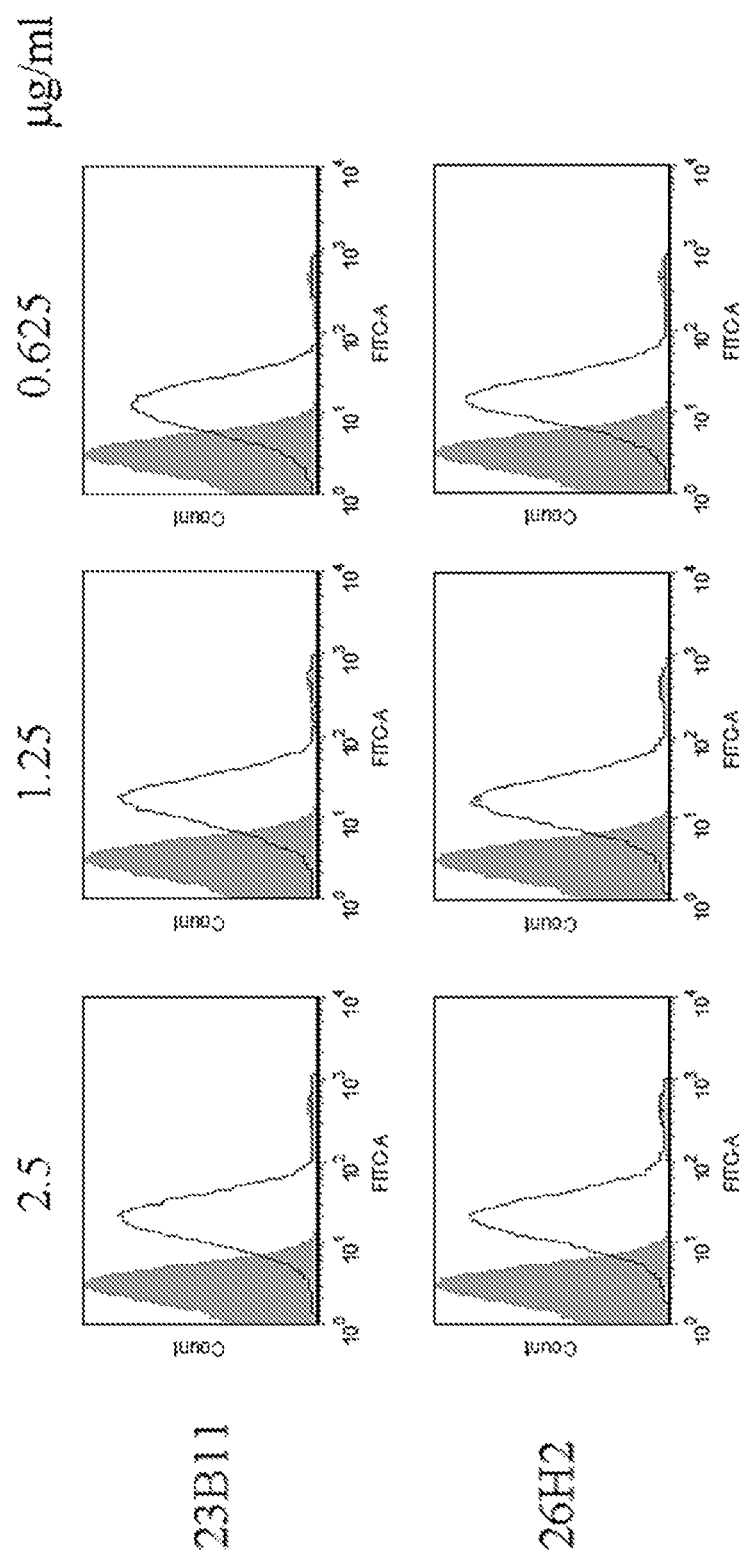

Ramos cell lines were used to study the binding of mAb 23B11 to mIgE-expressing B cells and the subsequent effects of such binding to the human B cells. The Ramos cells were respectively transfected with the long or short isoforms of human mIgE, thus expressing mIgE.Fc$_L$ and mIgE.Fc$_S$. The results of the fluorescence flow cytometric analysis show that mAb 23B11 binds to mIgE-expressing Ramos cells. See FIG. 2.

Figure 3:
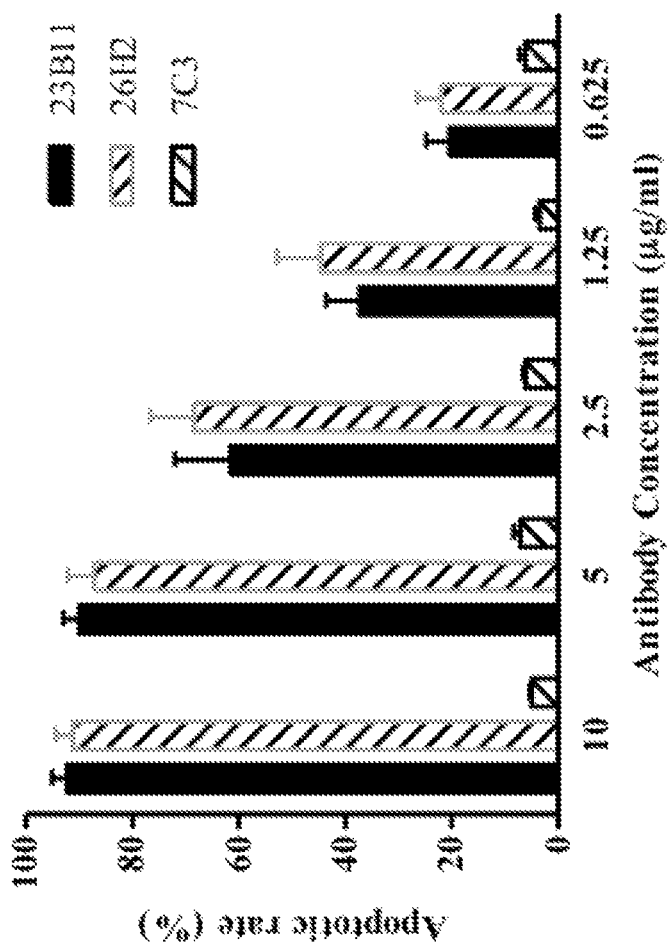
FIG. 3 is a graph showing the apoptotic rate of mIgE-expressing Ramos cells exposed to mAb 23B11. MAb 7C3, which is specific to migis-α (the extracellular segment of the C-terminal membrane-anchor peptide of membrane-bound α chain of IgA), was used as an isotype mAb control, and mAb 26H2 was used as a positive control. Results are presented as mean±SD of triplicates from three independent experiments.

Example 4: The mAb 23B11 Induces Apoptosis of mIgE-Expressing Ramos Transfectants To investigate whether 23B11 can cause the apoptosis of mIgE-expressing B cells, mIgE.Fc$_L$ or mIgE.Fc$_S$-expressing stable Ramos transfectants (5×10$^5$/ml) were incubated with purified mAb 23B11 in complete RPMI1640 medium for 1 hour at 37° C. Secondary antibody, goat F(ab')$_2$ specific for Fc of mouse IgG (Jackson ImmunoResearch Laboratories, West Grove, Pa.) was added into the medium at a final concentration of 25 μg/ml, and the cultures were incubated for an additional 20 hours at 37° C. The extent of the apoptosis of the treated cells was determined by detecting phosphatidylserine (PS) exposure. The results in FIG. 3 show that mAb 23B11 can induce apoptosis of mIgE-expressing Ramos cells.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or"

should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An isolated anti-IgE antibody that binds to AAGGSVPHPRCHCGAGRA (SEQ ID NO:1).

2. The isolated anti-IgE antibody of claim 1, which binds to SVPHPRCHCGAGRA (SEQ ID NO:4).

3. The isolated antibody of claim 1, wherein the antibody is a full-length antibody or an antigen-binding fragment thereof.

4. The isolated antibody of claim 3, wherein the antigen binding fragment is a Fab fragment, a F(ab')2 fragment, or a single-chain Fv fragment.

5. The isolated antibody of claim 1, wherein antibody is a human antibody, a humanized antibody, a chimeric antibody, or a single-chain antibody.

6. The isolated antibody of claim 1, wherein the antibody comprises a heavy chain variable region ($V_H$) that comprises a $V_H$ complementarity determining region (CDR) 1 set forth as SEQ ID NO:12, a $V_H$ CDR2 set forth as SEQ ID NO:13, and a $V_H$ CDR3 set forth as SEQ ID NO:14; and a light chain variable region ($V_L$) that comprises a $V_L$ CDR1 set forth as SEQ ID NO:15, a $V_L$ CDR2 set forth as SEQ ID NO:16, and a $V_L$ CDR3 set forth as SEQ ID NO:17.

7. The isolated antibody of claim 1, wherein the antibody comprises a $V_H$ that comprises the amino acid sequence of SEQ ID NO:8; and a $V_L$ that comprises the amino acid sequence of SEQ ID NO:9.

8. The isolated antibody of claim 7, wherein the antibody binds to the same epitope as an anti-IgE antibody having a $V_H$ set forth as SEQ ID NO:8 and a $V_L$ set forth as SEQ ID NO:9.

9. The isolated antibody of claim 8, wherein the antibody comprises a $V_H$ set forth as SEQ ID NO:8 and a $V_L$ set forth as SEQ ID NO:9.

10. An isolated nucleic acid or a set of nucleic acids, comprising a nucleotide sequence encoding an antibody heavy chain variable region ($V_H$) that comprises a $V_H$ complementarity determining region (CDR) 1 set forth as SEQ ID NO:12, a $V_H$ CDR2 set forth as SEQ ID NO:13, and a $V_H$ CDR3 set forth as SEQ ID NO:14; and a nucleotide sequence encoding an antibody light chain variable region ($V_L$) that comprises a $V_L$ complementarity determining region (CDR1) set forth as SEQ ID NO:15, a $V_L$ CDR2 set forth as SEQ ID NO:16, and a $V_L$ CDR3 set forth as SEQ ID NO:17.

11. A vector or a vector set, comprising the nucleic acid or the set of nucleic acids of claim 10.

12. The vector or vector set of claim 11, wherein the vector(s) is an expression vector.

13. A host cell comprising the vector(s) of claim 12.

14. A composition comprising the isolated antibody of claim 1.

15. The composition of claim 14, wherein the composition is a pharmaceutical composition comprising a pharmaceutically acceptable adjuvant and/or carrier.

16. An immune composition comprising a peptide and an adjuvant, wherein the peptide is AAGGSVPHPRCHCGAGRA (SEQ ID NO:1) or an immunogenic epitope therein.

17. A method of treating an IgE-mediated condition in a subject, the method comprising administering to a subject in need thereof an effective amount of the antibody of claim 1.

18. The method of claim 17, wherein the IgE-mediated condition is cold-induced urticaria, chronic urticaria, cholinergic urticaria, chronic rhinosinusitis, systemic mastocytosis, cutaneous mastocytosis, allergic bronchopulmonary aspergillosis, recurrent idiopathic angioedema, interstitial cystitis, an eosinophil-associated gastrointestinal disorder, allergic asthma, allergic rhinitis or atopic dermatitis.

19. The method of claim 18, wherein the IgE-mediated condition is allergic asthma, allergic rhinitis or atopic dermatitis.

20. The method of claim 17, wherein the subject is a human patient having or suspected of having an IgE-mediated condition.

21. A method for preparing an anti-IgE antibody, comprising:
culturing the host cell of claim 13 in a medium under conditions allowing for expression of the antibody, and collecting the cultured host cells for purification of the antibody.

22. The method of claim 21, further comprising isolating the antibody thus produced.

* * * * *

SEQUENCE LISTING

```
<160> NUMBER OF SEQ ID NOS: 44

<210> SEQ ID NO 1
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1

Ala Ala Gly Gly Ser Val Pro His Pro Arg Cys His Cys Gly Ala Gly
1               5                   10                  15

Arg Ala

<210> SEQ ID NO 2
<211> LENGTH: 52
<212> TYPE: PRT
<213> ORGANISM: Artificial Sequence
<220> FEATURE:
<223> OTHER INFORMATION: Synthetic Polypeptide

<400> SEQUENCE: 2

Gly Leu Ala Gly Gly Ser Ala Gln Ser Gln Arg Ala Pro Asp Arg Val
1               5                   10                  15

Leu Cys His Ser Gly Gln Gln Gln Gly Leu Pro Arg Ala Ala Gly Gly
                20                  25                  30

Ser Val Pro His Pro Arg Cys His Cys Gly Ala Gly Arg Ala Asp Trp
```

```
                       35                  40                  45
Pro Gly Pro Pro
    50

<210> SEQ ID NO 3
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 3

Gly Gly Ser Val Pro His Pro Arg Cys His Cys Gly Ala Gly Arg Ala
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 4

Ser Val Pro His Pro Arg Cys His Cys Gly Ala Gly Arg Ala
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 5

Pro Arg Ala Ala Gly Gly Ser Val Pro His Pro Arg Cys His
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 6

Gln Gln Gly Leu Pro Arg Ala Ala Gly Gly Ser Val Pro His Pro
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 7

Arg Ala Asp Trp Pro Gly Pro Pro
1               5

<210> SEQ ID NO 8
<211> LENGTH: 120
<212> TYPE: PRT
<213> ORGANISM: Mus musculus

<400> SEQUENCE: 8

Glu Val Gln Leu Gln Gln Ser Gly Ala Glu Leu Met Lys Pro Gly Ala
```

```
            1               5                  10                 15
Ser Val Lys Ile Ser Cys Lys Ala Ser Gly Tyr Thr Phe Ser Ser Tyr
            20                 25                 30

Trp Ile Glu Trp Val Tyr Gln Arg Pro Gly His Gly Leu Glu Trp Ile
            35                 40                 45

Gly Glu Ile Leu Pro Gly Ser Gly Ser Asn Tyr Asn Glu Lys Phe
            50                 55                 60

Glu Gly Lys Ala Thr Phe Thr Ala Asp Thr Ser Ser Asn Thr Ala Tyr
 65                70                 75                 80

Met His Leu Ser Ser Leu Thr Ser Glu Asp Ser Ala Val Tyr Tyr Cys
                   85                 90                 95

Ala Arg Trp Asp Tyr Tyr Gly Arg Gly Phe Asp Tyr Trp Gly Gln
                   100                105                110

Gly Thr Thr Leu Thr Ala Ala Ala
            115                120
```

<210> SEQ ID NO 9
<211> LENGTH: 112
<212> TYPE: PRT
<213> ORGANISM: Mus musculus

<400> SEQUENCE: 9

```
Asp Ile Val Met Thr Gln Ala Ala Pro Ser Val Pro Val Thr Pro Gly
 1               5                  10                 15

Glu Ser Val Ser Ile Ser Cys Arg Ser Ser Lys Ser Leu Leu His Ser
            20                 25                 30

Asn Gly Asn Ile Tyr Leu His Trp Phe Leu Gln Arg Pro Gly Gln Ser
            35                 40                 45

Pro Gln Leu Leu Ile Tyr Arg Met Ser Asn Val Ala Ser Gly Val Pro
            50                 55                 60

Asp Arg Phe Ser Gly Ser Gly Ser Gly Thr Val Phe Thr Leu Arg Ile
 65                70                 75                 80

Ser Arg Val Glu Ala Glu Asp Val Gly Val Tyr Tyr Cys Met Gln Asn
                   85                 90                 95

Leu Glu Tyr Pro Leu Thr Phe Gly Ala Gly Thr Lys Leu Glu Leu Lys
                   100                105                110
```

<210> SEQ ID NO 10
<211> LENGTH: 120
<212> TYPE: PRT
<213> ORGANISM: Mus musculus

<400> SEQUENCE: 10

```
Gln Val Gln Leu Gln Gln Ser Gly Ala Glu Leu Met Lys Pro Gly Ala
 1               5                  10                 15

Ser Val Lys Leu Ser Cys Lys Thr Ser Gly Tyr Thr Phe Thr Gly Tyr
            20                 25                 30

Trp Ile Glu Trp Val Lys Gln Arg Pro Gly His Gly Leu Glu Trp Ile
            35                 40                 45

Gly Glu Ile Leu Pro Gly Ser Gly Ser Thr Asn Tyr Asn Glu Lys Phe
            50                 55                 60

Lys Gly Lys Ala Thr Phe Thr Ala Asp Thr Ser Ser Asn Thr Ala Tyr
 65                70                 75                 80

Met Gln Leu Ser Ser Leu Thr Thr Glu Asp Ser Ala Ile Tyr Tyr Cys
                   85                 90                 95

Ala Arg Trp Asp Tyr Tyr Gly Gly Arg Gly Phe Asp Tyr Trp Gly Gln
```

```
                    100                 105                 110

Gly Thr Thr Leu Thr Ala Ala Ala
            115                 120

<210> SEQ ID NO 11
<211> LENGTH: 112
<212> TYPE: PRT
<213> ORGANISM: Mus musculus

<400> SEQUENCE: 11

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

<210> SEQ ID NO 12
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 12

Gly Tyr Thr Phe Ser Ser Tyr Trp
1               5

<210> SEQ ID NO 13
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 13

Ile Leu Pro Gly Ser Gly Ser Ser Asn Tyr Asn Glu Lys Phe Glu Gly
1               5                   10                  15

Lys

<210> SEQ ID NO 14
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 14

Trp Asp Tyr Tyr Gly Gly Arg Gly Phe Asp Tyr
1               5                   10

<210> SEQ ID NO 15
<211> LENGTH: 16
<212> TYPE: PRT
```

```
<213> ORGANISM: Artificial Sequence
<220> FEATURE:
<223> OTHER INFORMATION: Synthetic Polypeptide

<400> SEQUENCE: 15

Arg Ser Ser Lys Ser Leu Leu His Ser Asn Gly Asn Ile Tyr Leu His
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 16

Arg Met Ser Asn Val Ala Ser
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 17

Met Gln Asn Leu Glu Tyr Pro Leu
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 18

Ala Gly Gly Ser Val Pro His Pro Arg Cys His Cys Gly Ala Gly Arg
1               5                   10                  15

Ala

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Ala Gly Gly Ser Val
1               5

<210> SEQ ID NO 20
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 20

Gly Ser Val Pro His Pro Arg Cys His Cys Gly Ala Gly Arg Ala
1               5                   10                  15

<210> SEQ ID NO 21
<211> LENGTH: 4
```

```
<212> TYPE: PRT
<213> ORGANISM: Artificial Sequence
<220> FEATURE:
<223> OTHER INFORMATION: Synthetic Polypeptide

<400> SEQUENCE: 21

Ala Gly Gly Ser
1

<210> SEQ ID NO 22
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 22

Val Pro His Pro Arg Cys His Cys Gly Ala Gly Arg Ala
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 23

Pro His Pro Arg Cys His Cys Gly Ala Gly Arg Ala
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 24

His Pro Arg Cys His Cys Gly Ala Gly Arg Ala
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 25

Pro Arg Cys His Cys Gly Ala Gly Arg Ala
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 26

Arg Cys His Cys Gly Ala Gly Arg Ala
1               5

<210> SEQ ID NO 27
<211> LENGTH: 8
<212> TYPE: PRT
```

```
<213> ORGANISM: Artificial Sequence
<220> FEATURE:
<223> OTHER INFORMATION: Synthetic Polypeptide

<400> SEQUENCE: 27

Cys His Cys Gly Ala Gly Arg Ala
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 28

His Cys Gly Ala Gly Arg Ala
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 29

Cys Gly Ala Gly Arg Ala
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 30

Gly Ala Gly Arg Ala
1               5

<210> SEQ ID NO 31
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 31

Ala Gly Arg Ala
1

<210> SEQ ID NO 32
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 32

Ala Gly Gly Ser Val Pro His Pro Arg Cys His Cys Gly Ala Gly Arg
1               5                   10                  15

<210> SEQ ID NO 33
<211> LENGTH: 15
<212> TYPE: PRT
<213> ORGANISM: Artificial Sequence
```

<220> FEATURE:
<223> OTHER INFORMATION: Synthetic Polypeptide

<400> SEQUENCE: 33

Ala Gly Gly Ser Val Pro His Pro Arg Cys His Cys Gly Ala Gly
1               5                   10                  15

<210> SEQ ID NO 34
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 34

Ala Gly Gly Ser Val Pro His Pro Arg Cys His Cys Gly Ala
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 35

Ala Gly Gly Ser Val Pro His Pro Arg Cys His Cys Gly
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 36

Ala Gly Gly Ser Val Pro His Pro Arg Cys His Cys
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 37

Ala Gly Gly Ser Val Pro His Pro Arg Cys His
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 38

Ala Gly Gly Ser Val Pro His Pro Arg Cys
1               5                   10

<210> SEQ ID NO 39
<211> LENGTH: 9
<212> TYPE: PRT
<213> ORGANISM: Artificial Sequence
<220> FEATURE:

```
<223> OTHER INFORMATION: Synthetic Polypeptide

<400> SEQUENCE: 39

Ala Gly Gly Ser Val Pro His Pro Arg
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 40

Ala Gly Gly Ser Val Pro His Pro
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 41

Ala Gly Gly Ser Val Pro His
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 42

Ala Gly Gly Ser Val Pro
1               5

<210> SEQ ID NO 43
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 43

Gly Leu Pro Arg Ala Ala Gly Gly Ser Val Pro His Pro Arg Cys His
1               5                   10                  15

Cys Gly Ala Gly Arg Ala
            20

<210> SEQ ID NO 44
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 44

Ala Ala Gly Gly
1
```